(12) United States Patent
Martin et al.

(10) Patent No.: US 7,300,789 B2
(45) Date of Patent: Nov. 27, 2007

(54) BIOREACTOR FORMING A RIGID VESSEL

(75) Inventors: Richard Martin, Rochecorbon (FR); Pascal Hilaire, Vouvray (FR)

(73) Assignee: L'Oreal, Paris (FR)

( * ) Notice: Subject to any disclaimer, the term of this patent is extended or adjusted under 35 U.S.C. 154(b) by 670 days.

(21) Appl. No.: 10/442,297

(22) Filed: May 21, 2003

(65) Prior Publication Data

US 2004/0029267 A1 Feb. 12, 2004

Related U.S. Application Data

(60) Provisional application No. 60/398,567, filed on Jul. 26, 2002.

(30) Foreign Application Priority Data

May 21, 2002 (FR) .................... 02 06146

(51) Int. Cl.
*C12M 1/24* (2006.01)
(52) U.S. Cl. ............... 435/297.5; 435/298.2; 435/299.2; 435/304.2; 435/304.3
(58) Field of Classification Search ............ 435/297.5, 435/298.2, 299.1, 299.2, 304.1–304.3, 305.4, 435/297.2
See application file for complete search history.

(56) References Cited

U.S. PATENT DOCUMENTS 4,556,639 A * 12/1985 Izawa et al. ................ 435/379
4,734,373 A * 3/1988 Bartal ...................... 435/299.2
4,839,292 A * 6/1989 Cremonese .............. 435/297.2
5,047,347 A * 9/1991 Cline ....................... 435/297.1
5,310,676 A * 5/1994 Johansson et al. ....... 435/304.1
5,512,480 A * 4/1996 Sandstrom et al. ...... 435/289.1
5,650,325 A * 7/1997 Spielmann .............. 435/299.1
5,733,775 A 3/1998 Puchegger et al.
5,934,804 A * 8/1999 Branson et al. ............. 366/208

(Continued)

FOREIGN PATENT DOCUMENTS

DE 328362 10/1920

(Continued)

OTHER PUBLICATIONS

Tunnah et al. "Rocker Cell Culture Incubator." Biotechnology and Bioengineering. vol. X (1968), pp. 698-706/.*

(Continued)

*Primary Examiner*—William H. Beisner
(74) *Attorney, Agent, or Firm*—Oblon, Spivak, McClelland, Maier & Neustadt, P.C.

(57) ABSTRACT

The invention provides a bioreactor (10) for the culture of animal, vegetable, microbial of algal cells of their co-cultures, of the type including a body (12) which delimits an internal volume (14) capable of holding a culture liquid (16) and a gas volume (17) above the culture liquid (16), and which includes means for introducing (18) and/or extracting (20) elements respectively into and/or out of the internal volume (14) of the body (12), and of the type which includes means (22) for driving the body (12) in an oscillating movement so as to obtain agitation of the culture liquid (16), characterised in that the body (12) is a rigid vessel.

29 Claims, 3 Drawing Sheets

U.S. PATENT DOCUMENTS

| | | | |
|---|---|---|---|
| 6,066,497 A | 5/2000 | Powell | |
| 6,521,451 B2 * | 2/2003 | Potter | 435/383 |
| 6,777,227 B2 * | 8/2004 | Ricci et al. | 435/304.1 |
| 2001/0043508 A1 * | 11/2001 | Zhou | 366/273 |

FOREIGN PATENT DOCUMENTS

| | | |
|---|---|---|
| DE | 1812419 | 6/1970 |
| DE | 256868 | 5/1988 |
| FR | 2519020 | 7/1983 |
| GB | 474897 | 11/1937 |
| WO | WO 97/33972 | 9/1997 |
| WO | WO 00/66706 | 11/2000 |
| WO | WO 01/64844 | 9/2001 |

OTHER PUBLICATIONS

Wilbanks et al. "A Simple Rocker for Organ Culure." Journal of Tissue Culture Methods. vol. 8, No. 2 (1983), pp. 69-71.*

Malin et al. Use of a dynamic in vitro attachment and invasion system (DIVAS) to determine influence of growth rate on invasion of respiratory epithelial cells by group B Streptococcus, PNAS. vol. 98, No. 23 (Nov. 6, 2001), pp. 13335-13340.*

Patent Abstracts of Japan vol. 1998, No. 12—JP 10 191959, Jul. 28, 1998.

* cited by examiner

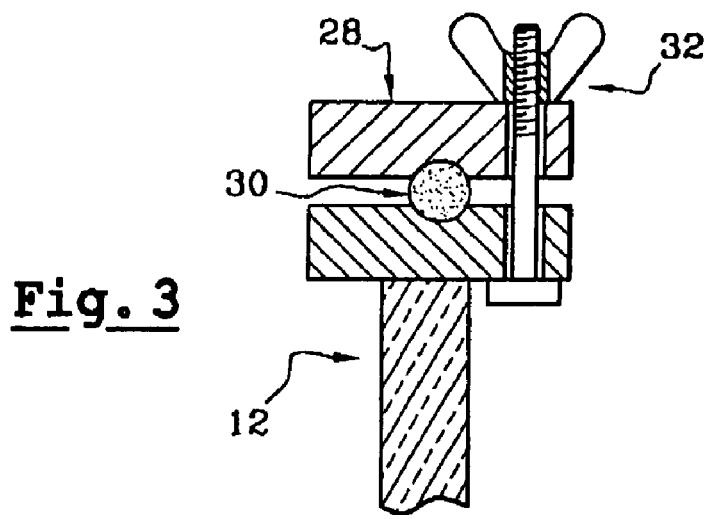
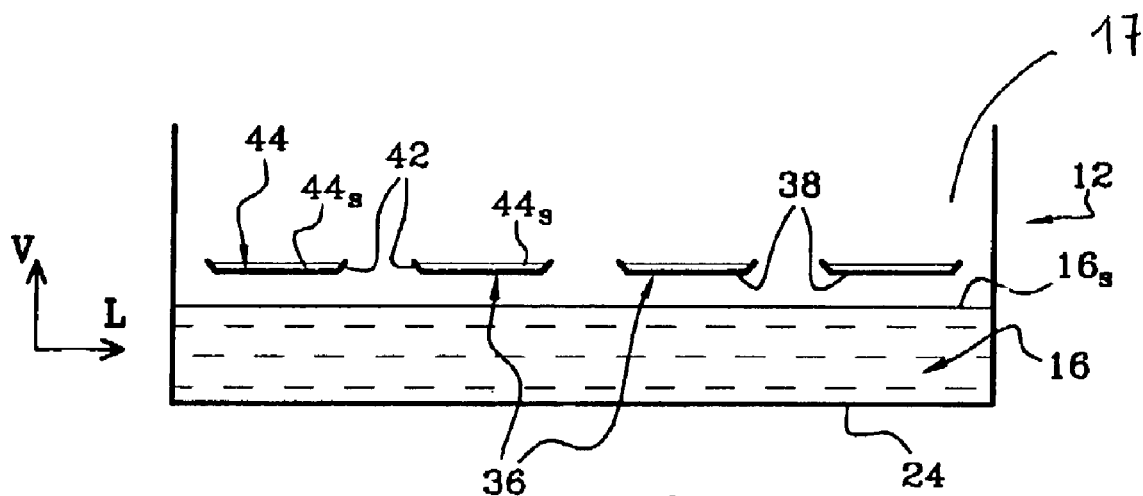
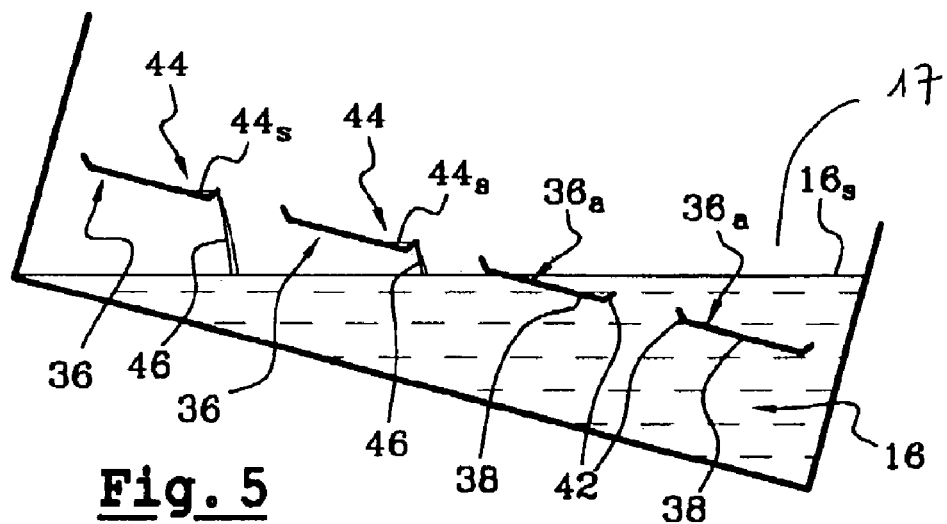

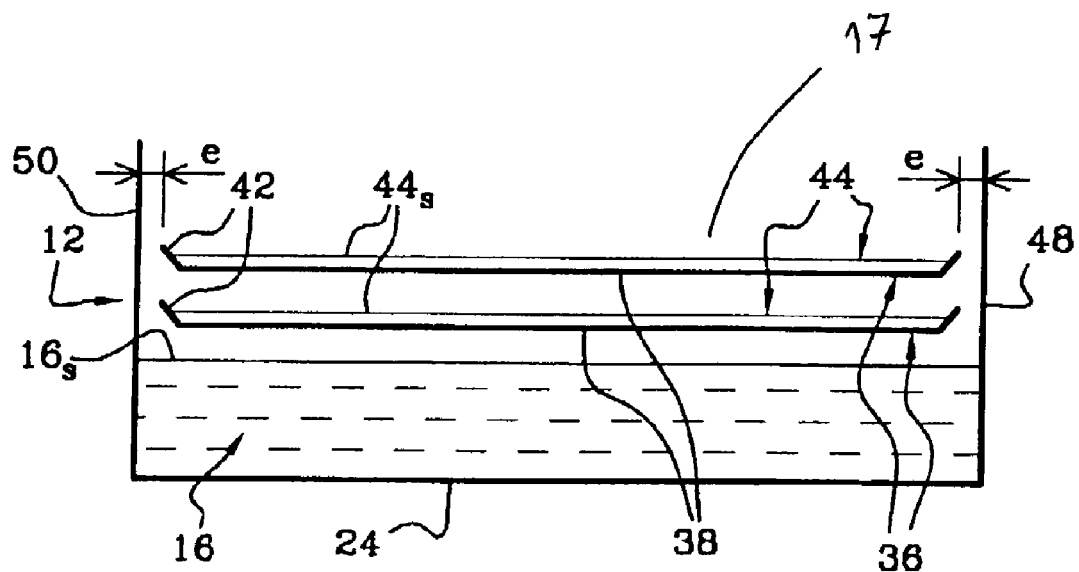
Fig. 6
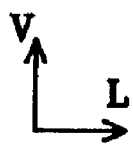
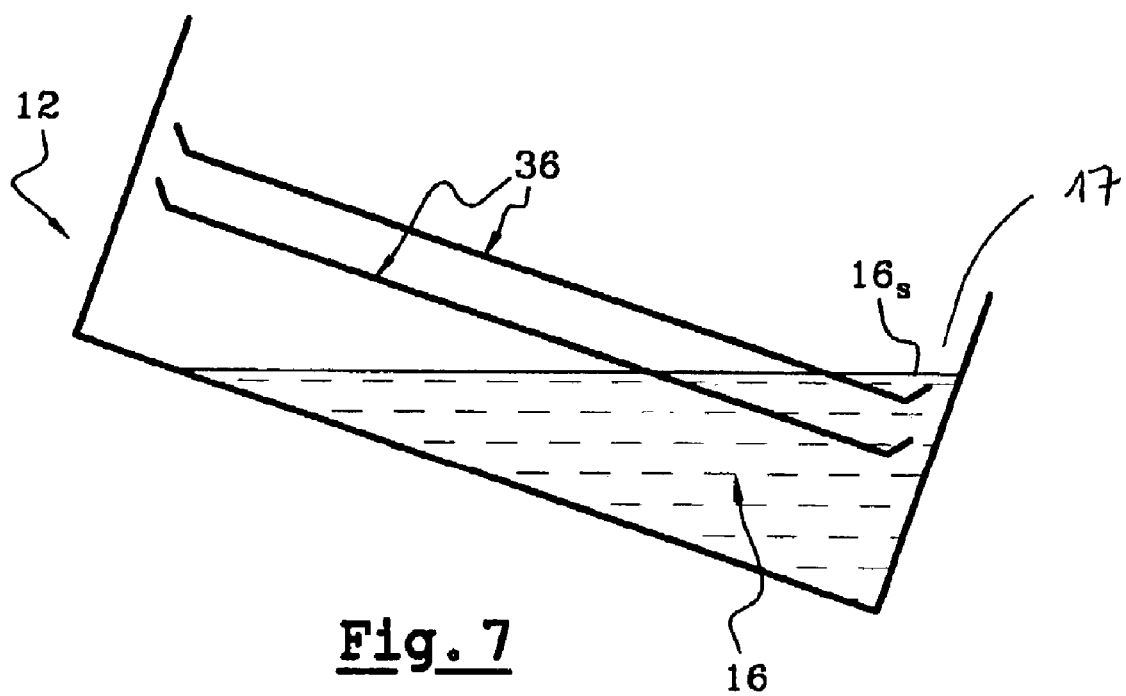
Fig. 7

BIOREACTOR FORMING A RIGID VESSEL

CROSS-REFERENCE TO RELATED APPLICATIONS

This document claims priority to French Application No. 02 06146, filed May 21, 2002 and U.S. Provisional Application No. 60/398,567, filed Jul. 26, 2002, the entire content of which is hereby incorporated by reference.

FIELD OF THE INVENTION

The invention provides a bioreactor for a culture of animal, vegetable, microbial or algal cells, of the type including a body which delimits an internal volume capable of holding a culture liquid and a gas volume above the culture liquid, and which includes an arrangement for introducing and/or extracting elements respectively into and/or out of the internal volume of the body. The bioreactor further includes a drive to move the body for oscillating movement so as to agitate the culture liquid.

BACKGROUND OF THE INVENTION

DISCUSSION OF BACKGROUND

The technological advances in the field of biotechnology are leading to an increase in the demands for animal, vegetable, microbial or algal cells, so that it is necessary to increase the production capacities for these cells.

Production of the cells is carried out by cultivating them in a culture liquid which includes components necessary for their growth and which may be brought into contact with a gas which also contains components necessary for the growth of the cells. In particular, so-called "aerobic" cells are brought into contact with oxygen in air, which is a component necessary for their development, by an arrangement for injecting air into the culture liquid. The culture liquid can also be agitated by an agitation arrangement in order to optimize the contact between the cells and the components necessary for their growth which are contained in the liquid and/or in the gas.

For the culture of cells under such conditions, it has been proposed to use vessels which are made of stainless steel complying with food requirements, with the designation Z2 CND17.12 (standard NF A02-004) or 316L (AISI standard), and in which the culture liquid is agitated by an internal agitator, for example of the paddle type. However, the culture of certain categories of cells, referred to as "phototropic," requires significant illumination of the culture liquid, and vessels made of stainless steel only make it possible to provide relatively weak illumination of the culture liquid. Further, the use of an internal agitator causes "shearing" of the culture liquid, which damages the cells and slows their development.

It has also been proposed to cultivate cells in a bioreactor composed of a plurality of flasks, or bottles, which have horizontal axes and are arranged in a rotor that can be moved in continuous rotation about a horizontal axis, as described and represented in U.S. Pat. No. 6,066,497. Each bottle includes an arrangement to allow injection or withdrawal of certain products, respectively into or out of their internal volume. The dimensions of the bottles are small so that a person can transport them without difficulty. However, the bottles therefore have a relatively restricted maximum capacity. In addition, the bottles can be used only with a minimum quantity of liquid, so that it is relatively difficult to modify the quantity of culture liquid during culture. However, when it is desired to inject a product into the culture liquid, it is necessary to carry out one injection for each bottle, which multiplies the contamination risk of the liquid by the number of bottles.

Finally, as described in Document FR-A-2,519,020, it has also been proposed to cultivate the cells in a bioreactor which includes a more or less translucent plastic bag fitted on a plate driven in a seesaw movement. The bag is partially filled with the culture liquid, and the volume of the bag is made up by injecting air so as to allow gas to exchange between the gas and the cells. However, the air which is introduced into the bioreactor needs to be sterile, such that the bioreactor requires complex air-sterilization system which can be relatively expensive. In addition, the pressure exerted by the culture liquid on the walls of the bag naturally tends to make it adopt a substantially spherical shape, which, as is known, is the geometrical shape which makes it possible to have a minimum external surface area for a maximum internal volume. However, this configuration reduces the free surface area of the culture liquid which is in contact with the air.

SUMMARY OF THE INVENTION

It is an object of the invention to provide a bioreactor which makes it possible to have a larger free contact surface area of the culture liquid with the air present in the bioreactor for a given volume of culture liquid.

In accordance with a preferred form, the invention provides a bioreactor in which the body is a rigid vessel.

The preferred form of the invention can also include the following additional advantageous features alone or in combination:

the body can be made of a material which is permeable to light;

the body can include an arrangement for increasing the surface area of the culture liquid which is in contact with the gas volume present in the upper part of the body;

the bioreactor can include at least one container which is open at the top, which is arranged inside the body and driven to move with the body and which, for at least one orientation of the body, is capable of isolating a certain quantity of culture liquid from the rest of the culture liquid contained in the body;

the bioreactor can include at least one air filter allowing gas exchange between the internal volume of the body and the outside;

the upper face of the body is at least partially open, and the upper face of the body can be closed in a sterile manner by a closure element;

the closure element can be a film which is permeable to air so as to form an air filter, or the closure element can be a lid which carries the filter and the arrangement for introduction and/or extraction of elements;

the body can be driven in an oscillating movement about a substantially horizontal axis;

the body can be driven in an alternating translation motion parallel to a substantially horizontal direction.

BRIEF DESCRIPTION OF THE DRAWINGS

Other characteristics and advantages of the invention will become apparent from the following detailed description, particularly when considered in conjunction with the drawings in which:

FIG. 3 is a detailed view on a larger scale of an arrangement for locking the closure element of the body;

FIG. 4 is a side view of the body represented in FIG. 1, in which the body is represented in its resting position;

FIG. 5 is a view similar to that in FIG. 4, in which the body is represented during an oscillation;

FIG. 6 is a view similar to that in FIG. 4, representing an alternative embodiment of the invention in which the body includes containers, each of which extends substantially over the full length of the body;

FIG. 7 is a view similar to that in FIG. 5, according to the alternative embodiment of the invention.

DETAILED DESCRIPTION OF THE PREFERRED EMBODIMENTS

Figure 1:
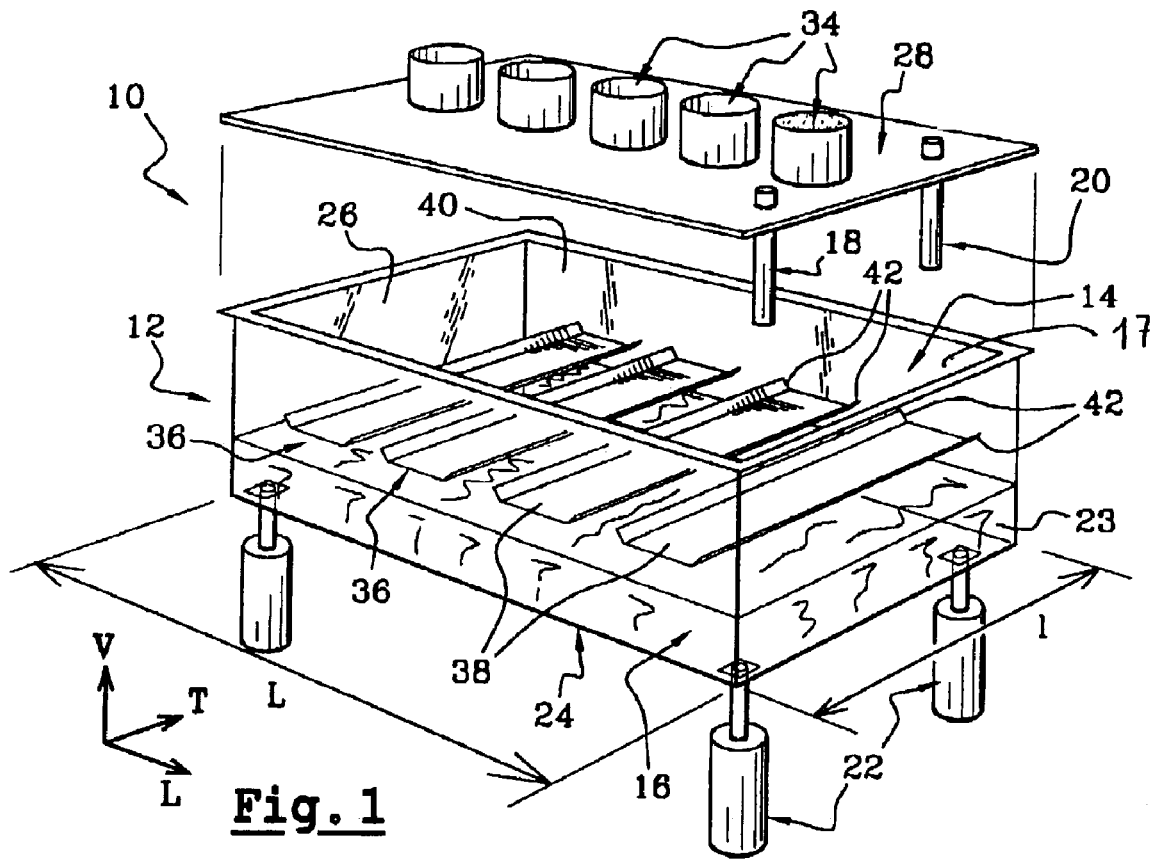
FIG. 1 is a schematic perspective representation of a bioreactor according to the teachings of the invention.

Referring now to the drawings, non-limiting examples of embodiments of the invention will now be described. For reference purposes in the drawings, the vertical, longitudinal and transverse orientations according to the coordinate system V, L, T are indicated in the figures. Identical, similar or analogous elements will be denoted by the same reference numerals in the description which follows.

FIG. 1 represents a bioreactor 10 for the culture of, for example, animal, vegetable, microbial or algal cells, which includes a body 12 preferably made of a rigid material capable of transmitting light and delimiting, inside the vessel, a volume 14 intended to hold a culture liquid 16. In use, the culture liquid 16 constitutes the medium in which the cells develop, and it contains nutrient elements necessary for the growth of the cells. A volume of gas 17, for example air in the event that the cells being cultivated are "aerobic cells," is present above the culture liquid 16.

One parameter which influences the performance of the bioreactor 10 is the concentration of the cells in the culture liquid 16, which must lie within a given range of values. Since the purpose of the bioreactor 10 is to produce cells, it is necessary to replenish and/or top off the culture liquid with a fresh culture liquid as they multiply. To this end, the illustrated bioreactor 10 includes an arrangement such as a conduit or passage shown at 18 for introducing elements into the internal volume 14 of the body 12, in particular fresh culture liquid, which are designed so that the introduction of the fresh culture liquid takes place without introducing polluting foreign elements into the internal volume 14 of the body. The bioreactor 10 also includes an arrangement such as a conduit or passage 20 for extracting elements from the internal volume 14 of the body 12, which are used in particular for withdrawing a small quantity of culture liquid 16, for example, to allow an analysis to make it possible to check that the culture of the cells is proceeding correctly.

In the illustrated embodiment, the body 12 is driven in an alternating movement making it possible to obtain continuous or periodic mixing of the culture liquid 16. This mixing of the culture liquid 16 makes it possible to ensure the gas exchanges between the cells and the gas 17 present above the liquid, in particular with the oxygen contained in air when culturing so-called "aerobic cells." In addition, the mixing of the culture liquid 16 makes it possible to optimize the contact between the cells and the nutrient elements contained in the culture liquid 16, and such an external agitation system makes possible to avoid any shearing of the culture liquid.

When the body 12 is driven in an alternating movement, the presence of the gas volume above the culture liquid 16 makes it possible to form turbulence or movement, which leads to the formation of waves (not shown). The result of this turbulence is that the cells are driven in a stirring movement in the culture liquid, at least one component of which is vertical, and therefore, a continuous change of the cells which are at the surface 16s of the culture liquid 16, hence increasing the gas exchanges or interaction with the gas in the internal volume.

In the embodiment represented in FIG. 1, the bioreactor includes a set of actuators 22, here arranged below the body 12, which drive it in an oscillating movement about a horizontal transverse axis. The oscillating movement of the body 12 may be obtained by any other means or expedients as would be recognized by persons skilled in the art. For example, Document WO-A-00,66706, describes a bioreactor that includes an oscillation plate on which the body is fitted.

Figure 2:
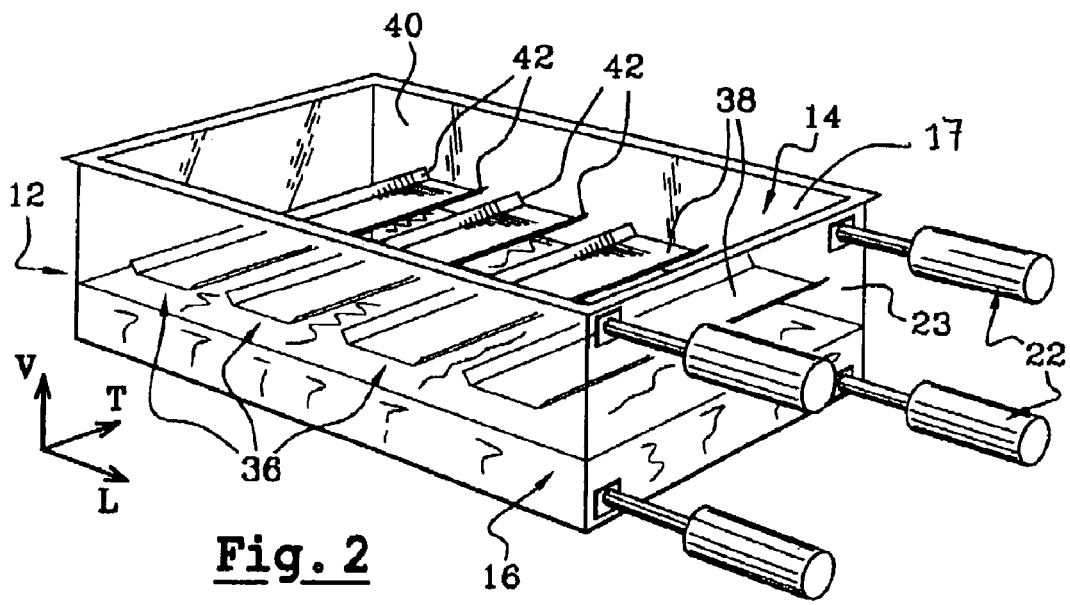
FIG. 2 is a view similar to that in FIG. 1, in which the body is driven in an alternating horizontal translation movement.

According to a variant which is represented in FIG. 2, the body or vessel 12 is driven in an alternating translation motion parallel to a horizontal longitudinal direction. The actuators are then oriented parallel to the direction of the movement, that is to say parallel to the longitudinal direction, and they can act on a vertical side wall 23 of the body 12.

In order to improve the yield of the bioreactor, the free upper surface area 16s of the liquid 16, which is in contact with the gases 17 contained in the internal volume 14 of the body 12, needs to be as large as possible so as to increase the volume of the natural gas exchanges or interaction between the culture liquid 16 and the gas volume 17, and also to allow movement of the liquid permitting it to be stirred. To this end, and according to the invention, the body 12 is preferably a rigid vessel. In the illustrated embodiment, the body has a rectangular parallelepiped shape. With this arrangement, when the body is in a resting position, it includes a horizontal rigid bottom 24 of longitudinal overall orientation and rigid vertical side walls 23.

According to an alternative embodiment (not shown), the body 12 includes a rigid frame. The bottom 24 and the side walls 23 are made of a flexible material, and they are held in shape by the frame.

Since the body 12 is rigid, the surface area 16s of the culture liquid 16 is substantially constant for a given position of the vessel, regardless of the volume of culture liquid 16 present inside the body 12. By contrast, with bioreactors in which the body is a flexible bag, the walls deform under the pressure exerted by the fluid, so that the surface area of the culture liquid which is in contact with the gases is then reduced.

In order to promote the growth of so-called "phototropic" cells, which need a great deal of light in order to be able to develop, the body 12 can be advantageously made of a rigid material which is permeable to light. This material is preferably a transparent polymer such as polycarbonate. One advantage of polycarbonate is it that can withstand temperatures of up to about 135° C., so that the body 12 can be sterilized in an autoclave. Sterilization of the body 12 is then greatly simplified compared with the sterilization of bioreactors for which it is carried out with steam and in situ, with complex and expensive assembly.

The upper face 26 of the body 12 is open, and allows the introduction 18 and the extraction 20 arrangements to pass therethrough. However, the culture of the cells requires a rigorous absence of foreign cells, so that the upper face 26 needs to be closed off to guarantee sterility of the bioreactor 10. To this end, the bioreactor 10 preferably includes a closure element 28 which covers the upper face 26, so that the internal volume 14 of the body 12 is protected from any external contamination.

In order for the closure of the upper face 26 to be leaktight and therefore sterile, the bioreactor 10 can include a seal. An example of a seal arrangement is shown in FIG. 3 in which a seal is interposed between the closure element 28 and the body 12, with the seal compressed by a locking arrangement 32. The locking or clamping arrangement 32, which here includes a screw-nut system, makes it possible to clamp or compress the seal 30 and to lock the closure element 28 in position. Preferably, the locking arrangement is arranged outside of the body 12 so that operation of the lock or clamp does not lead to contamination. Although a screw-nut locking/clamping arrangement is illustrated, it is to be understood that other locking/clamping arrangements can be used in accordance with the invention.

Due to the gas exchange between the cells and the air, it is necessary to constantly or regularly replenish the air which is present in the internal volume 14 of the body 12. Replenishment of the air can be achieved by way of air filters 34 including, for example, a micropore membrane which lets through only molecules or atoms contained in the air, and which prevents the passage of any other cell which could contaminate the culture liquid 16. Such filters permit so-called "passive" aeration, which does not perturb the gas equilibrium inside the bioreactor 10, in contrast to the air-injection systems used in traditional bioreactors.

According to a first embodiment represented schematically in the figures, the closure element 28 is a rigid lid which carries the introduction 18 and the extraction 20 arrangements, and which carries a plurality of air filters 34.

According to a second embodiment (not shown), the closure element 28 includes a film or a membrane which fully covers the upper face 26 of the body, and which is formed to have the same characteristics as the air filters 34, that is to say letting through only the molecules and atoms contained in the gas, while preventing the passage of elements which may contaminate the culture liquid 16.

The area of the surface 16s of the culture liquid 16 is limited by the dimensions of the body, in other words, by its length "L" and its width "l".

In order to increase the surface area of culture liquid 16 which is in contact with the air, and according to an alternative embodiment or optional aspect of the invention, the body 12 can include a plurality of containers 36 which, in the illustrated embodiments, include concave elements open at the top in the general shape of bowls or dishes. Each container illustrated includes a horizontal transverse plate 38 which joins together the two vertical longitudinal walls 40 of the body 12 and the transverse end edges or walls 42 which are inclined upwards.

The containers 36 are arranged to extend above the culture liquid 16 when the body 12 is in its resting position represented in FIG. 4. They are thus arranged so that at least some of the containers 36 are immersed in the culture liquid 16 in at least one position of the body 12 other than its resting position, in particular during the oscillating movement of the body, as represented in FIG. 5.

In the illustrated embodiment, a first movement of the body represented in FIG. 5, immerses first containers 36a in the liquid. When the body 12 pivots about its oscillation axis in order to return to its resting position, these first containers 36a have each taken up a certain quantity of culture liquid 44, and they then isolate it from the rest of the culture liquid 16. Gas exchanges can thereby take place at the level of the surface 16s of the culture liquid, and at the level of the surface 44s of the quantity of withdrawn liquid 44 temporarily stored in each container 36. The total exchange surface area is therefore increased.

When the body 12 tilts to the opposite position from that represented in FIG. 5, it is inclined with respect to its resting position, the first containers 36a extend above the culture liquid 16, and some (e.g., as represented at 46) of the quantity of withdrawn liquid 44 pours out of the first containers 36a into the rest of the culture liquid 16. The quantity 46 which pours out of the containers makes it possible to increase the total surface area of the culture liquid owing to its own surface area.

When the body 12 returns to the position in which the first containers 36a are immersed, the quantity of withdrawn culture liquid 44 is re-introduced and mixes in with the rest of the culture liquid 16. Combined with the stirring or agitating of the culture liquid 16, the action of the containers 36 makes it possible to increase the gas exchange surface area of the culture liquid 16.

According to a variant (not shown) of the invention, the body 12 can include a plurality of series or rows of containers 36 which are arranged at different distances from the bottom 24, so that at least some of the containers 36 are effective regardless of the depth of the culture liquid 16 contained in the body 12. Thus, plural containers can be provided at different horizontal and vertical positions within the body 12.

According to an alternative embodiment of the invention represented in FIGS. 6 and 7, the body 12 includes a plurality of containers 36 distributed at different distances from the bottom 24, and each container 36 is arranged at a different distance from the bottom 24 than the other containers 36. The length of each container 36 is preferably sufficiently less than the length "L" of the body 12, so that the surface area of the withdrawn quantity of culture liquid 44 is as large as possible, while leaving a space "e" between the container 36 and the front 48 and rear 50 transverse walls. Preferably, for the culture of "phototropic" cells, the containers 36 are made of the same transparent material as the body, so that they do not reduce the illumination of all the cells.

The bioreactor 10 makes it possible to add fresh culture liquid to the culture liquid 16, without needing to interrupt the culture of the cells. In this way, the overall level of the culture liquid 16 inside the body 12 can be increased with each addition of fresh culture liquid.

As should be apparent, simple mechanical rearrangements or modifications are possible to provide alternative embodiments of the invention. For example, the introduction 18 and extraction 20 arrangements may be provided on a vertical wall of the body 12.

A bioreactor according to the invention may also have a small quantity of cells at the start of the culture, for example 1 liter, which is transferred into a suitable volume of medium, for example 10 liters. Fresh culture liquid can be subsequently added as the cells grow, until reaching the maximum capacity of the bioreactor, for example 100 liters, without having to relocate the culture liquid from one bioreactor to another, hence limiting the contamination risk.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A bioreactor for the culture of animal, vegetable, microbial or algal cells comprising:
   a body which delimits an internal volume capable of holding a culture liquid and a gas volume above the culture liquid;
   at least one of means for introducing elements into and means for extracting elements from the internal volume of the body;
   means for driving the body in an oscillating movement so as to agitate the culture liquid; and a plurality of open containers open toward a top of the bioreactor and disposed at different horizontal positions, said plurality of open containers connected so as to move with the body and including spaces between the open containers in a horizontal direction and through which spaces the culture liquid may pass, wherein the body is a rigid vessel with an upper face which is at least partially open and permeable to air while the body is oscillated.

2. A bioreactor according to claim 1, wherein the body is at least partially formed of a material which is permeable to light.

3. A bioreactor according to claim 1, wherein the is plurality of open containers are arranged inside the body and driven to move with the body and further wherein for at least one orientation of the body the at least one container is capable of isolating a quantity of culture liquid from other portions of the culture liquid contained in the body.

4. A bioreactor according to claim 1, further including at least one air filter allowing gas exchange between the internal volume of the body and outside the body.

5. A bioreactor according to claim 4, wherein the upper face of the body is sterilely closed by a closure element permeable to air.

6. A bioreactor according to claim 1, wherein the upper face of the body is sterilely closed by a closure element permeable to air.

7. A bioreactor according to claim 6, wherein the closure element is a film which is permeable to air so as to form an air filter.

8. A bioreactor according to claim 6, wherein the closure element is a lid which carries a filter and the at least one of means for introducing elements and means for extracting elements.

9. A bioreactor according to claim 1, wherein the means for driving the body in an oscillating movement drives the body to move about a substantially horizontal axis.

10. A bioreactor as recited in claim 1, wherein at least one container inside the rigid vessel is completely separated from the culture liquid resting in contact with the body when the culture liquid is not agitated.

11. A bioreactor for the culture of animal, vegetable, microbial or algal cells comprising:
  a body which delimits an internal volume capable of holding a culture liquid and a gas volume above the culture liquid;
  at least one of means for introducing elements into and means for extracting elements from the internal volume of the body;
  means for driving the body in an oscillating movement so as to agitate the culture liquid; and
  a plurality of open containers open toward a top of the bioreactor and disposed at different horizontal positions, said plurality of open containers connected so as to move with the body and including spaces between the open containers in a horizontal direction and through which spaces the culture liquid may pass,
  wherein the body is a rigid vessel, and the means for driving the body drives the body to move in a reciprocating movement parallel to a substantially horizontal direction.

12. A bioreactor as recited in claim 11, wherein said plurality of open containers are formed with a material that is permeable to light.

13. A bioreactor comprising:
  a body which delimits an internal volume capable of holding a culture liquid and a gas volume above the culture liquid, wherein the body has a rigid structure with an opening at a top permeable to air while the body is oscillated;
  at least one drive device coupled to the body at a location outside of the body so as to move the body and agitate the culture liquid inside of the body;
  at least one access arrangement through which elements can be introduced into the body or removed from the body; and
  a plurality of open containers open toward a top of the bioreactor and disposed at different horizontal positions, said plurality of open containers connected so as to move with the body and including spaces between the open containers in a horizontal direction and through which spaces the culture liquid may pass.

14. A bioreactor as recited in claim 13, wherein the body is at least partially formed of a material which is permeable to light.

15. A bioreactor as recited in claim 13, wherein at least one of the open containers includes a material that is permeable to light.

16. A bioreactor as recited in claim 13, wherein said plurality of open containers include containers disposed at different vertical positions.

17. A bioreactor as recited in claim 13, wherein said plurality of containers are formed with a material that is permeable to light.

18. A bioreactor as recited in claim 17, wherein said at least one drive device drives said body in an oscillating movement.

19. A bioreactor as recited in claim 13, wherein said at least one drive device moves said body between at least a first position and a second position, and wherein in said first position culture liquid can flow between at least one container of the plurality of open containers and a bottom portion of said body.

20. A bioreactor as recited in claim 13, further including at least one filter through which gas can pass between an interior and an exterior of said body.

21. A bioreactor as recited in claim 20, wherein said at least one filter provides for passive gas movement.

22. A bioreactor as recited in claim 20, wherein said at least one filter includes a permeable film that closes at least a portion of said body.

23. A bioreactor as recited in claim 20, wherein said body includes a lid for closing said opening, and wherein said at least one filter is mounted to said lid.

24. A bioreactor as recited in claim 13, wherein said at least one drive device moves said body in a horizontal direction.

25. A bioreactor as recited in claim 13, wherein said at least one drive device moves said body about a horizontal axis.

26. A bioreactor as recited in claim 13, wherein the containers positioned at different horizontal positions are disposed at a same vertical level.

27. A bioreactor as recited in claim 13, wherein the at least one drive device comprises plural linear drive actuators.

28. A bioreactor as recited in claim 27, wherein the plural linear drive actuators are disposed on a same planar face of the body.

29. A bioreactor as recited in claim 28, wherein the body has a rectangular parallel-piped shape.

* * * * *